(12) United States Patent
Kwak et al.

(10) Patent No.: US 7,879,074 B2
(45) Date of Patent: Feb. 1, 2011

(54) POSTERIOR DYNAMIC STABILIZATION SYSTEMS AND METHODS

(75) Inventors: SeungKyu Daniel Kwak, Raynham, MA (US); Andrea Burke, Hudson, MA (US); Amie Borgstrom, San Francisco, CA (US); John Riley Hawkins, Raynham, MA (US); William Dunbar, Bethlehem, CT (US)

(73) Assignee: Depuy Spine, Inc., Raynham, MA (US)

( * ) Notice: Subject to any disclaimer, the term of this patent is extended or adjusted under 35 U.S.C. 154(b) by 69 days.

(21) Appl. No.: 11/162,880

(22) Filed: Sep. 27, 2005

(65) Prior Publication Data

US 2007/0073289 A1 Mar. 29, 2007

(51) Int. Cl.
*A61B 17/70* (2006.01)
(52) U.S. Cl. .................. 606/257; 606/254; 606/255
(58) Field of Classification Search ... 623/17.11–17.16; 606/61, 246–259
See application file for complete search history.

(56) References Cited

U.S. PATENT DOCUMENTS

| 457,964 | A | 8/1891 | Bolte |
|---|---|---|---|
| 2,638,301 | A | 2/1953 | Smith |
| 3,752,203 | A | 8/1973 | Hill, Jr. |
| 4,011,602 | A | 3/1977 | Rybicki et al. |
| 4,085,744 | A | 4/1978 | Lewis et al. |
| 4,179,905 | A | 12/1979 | Schultenkamper et al. |
| 4,289,124 | A | 9/1981 | Zickel |
| 4,404,967 | A | 9/1983 | Bacal et al. |
| 4,411,259 | A | 10/1983 | Drummond |
| 4,611,580 | A | 9/1986 | Wu |
| 4,611,581 | A | 9/1986 | Steffee |
| 4,611,582 | A | 9/1986 | Duff |
| 4,641,636 | A | 2/1987 | Cotrel et al. |
| 4,648,388 | A | 3/1987 | Steffee |
| 4,653,481 | A | 3/1987 | Howland et al. |
| 4,655,199 | A | 4/1987 | Steffee |
| 4,658,809 | A | 4/1987 | Ulrich et al. |
| 4,696,290 | A | 9/1987 | Steffee |

(Continued)

FOREIGN PATENT DOCUMENTS

DE 3219575 12/1983

(Continued)

OTHER PUBLICATIONS

"Materials—Biocompatible non-fouling PEO coating for biomaterials." Biomedical Materials. International Newsletters. 1994. HighBeam Research. May 21, 2009 <http://www.highbeam.com>.*

(Continued)

*Primary Examiner*—Thomas C Barrett
*Assistant Examiner*—Andrew Yang

(57) ABSTRACT

Various methods and devices are provided for stabilizing adjacent vertebrae in a patient's spinal column. In one exemplary embodiment, a spinal stabilization device is provided having a first cross-connector that is adapted to mate to opposed lateral sides of a first vertebra, a second cross-connector that is adapted to mate to opposed lateral sides of a second vertebra, and a flexible member that is coupled to the first and second cross-connectors and that is adapted to allow movement between first and second adjacent vertebrae coupled to the first and second cross-connectors.

14 Claims, 12 Drawing Sheets

U.S. PATENT DOCUMENTS

| | | | |
|---|---|---|---|
| 4,719,905 A | 1/1988 | Steffee | |
| 4,743,260 A | 5/1988 | Burton | |
| 4,759,769 A * | 7/1988 | Hedman et al. | 623/17.13 |
| 4,763,644 A | 8/1988 | Webb et al. | |
| 4,771,767 A | 9/1988 | Steffee | |
| 4,773,402 A | 9/1988 | Asher et al. | |
| 4,805,602 A | 2/1989 | Puno et al. | |
| 4,815,453 A | 3/1989 | Cotrel et al. | |
| 4,887,595 A | 12/1989 | Heinig et al. | |
| 4,913,134 A | 4/1990 | Luque et al. | |
| 4,950,269 A | 8/1990 | Gaines, Jr. | |
| 4,957,495 A | 9/1990 | Kluger et al. | |
| 5,002,542 A | 3/1991 | Frigg | |
| 5,005,562 A | 4/1991 | Cotrel et al. | |
| 5,010,879 A | 4/1991 | Moriya et al. | |
| 5,024,213 A | 6/1991 | Asher et al. | |
| 5,030,220 A | 7/1991 | Howland | |
| 5,067,955 A | 11/1991 | Cotrel et al. | |
| 5,084,049 A | 1/1992 | Asher et al. | |
| 5,092,866 A | 3/1992 | Breard | |
| 5,092,893 A | 3/1992 | Smith | |
| 5,102,412 A | 4/1992 | Rogozinski | |
| 5,113,685 A | 5/1992 | Asher et al. | |
| 5,116,334 A | 5/1992 | Cozad et al. | |
| 5,120,171 A | 6/1992 | Lasner | |
| 5,127,912 A | 7/1992 | Ray et al. | |
| 5,129,900 A | 7/1992 | Asher et al. | |
| 5,133,716 A * | 7/1992 | Plaza | 606/250 |
| 5,147,359 A | 9/1992 | Cozad et al. | |
| 5,147,360 A | 9/1992 | Dubousset et al. | |
| 5,154,718 A | 10/1992 | Cozad et al. | |
| 5,176,678 A | 1/1993 | Tsou | |
| 5,176,680 A | 1/1993 | Vignaud et al. | |
| 5,282,863 A | 2/1994 | Burton | |
| 5,387,213 A | 2/1995 | Breard et al. | |
| 5,415,661 A * | 5/1995 | Holmes | 606/69 |
| 5,458,642 A * | 10/1995 | Beer et al. | 623/17.13 |
| 5,474,086 A | 12/1995 | McCormick et al. | |
| 5,540,688 A | 7/1996 | Navas | |
| 5,556,431 A | 9/1996 | Buttner-Janz | |
| 5,562,737 A | 10/1996 | Graf | |
| 5,571,191 A | 11/1996 | Fitz | |
| 5,672,175 A | 9/1997 | Martin | |
| 5,876,403 A | 3/1999 | Shitoto et al. | |
| RE36,221 E | 6/1999 | Breard et al. | |
| 5,961,516 A | 10/1999 | Graf | |
| RE36,758 E | 6/2000 | Fitz | |
| 6,132,464 A | 10/2000 | Martin | |
| 6,267,764 B1 | 7/2001 | Elberg | |
| 6,273,888 B1 | 8/2001 | Justis | |
| 6,419,703 B1 | 7/2002 | Fallin et al. | |
| 6,440,169 B1 * | 8/2002 | Elberg et al. | 623/17.16 |
| 6,551,318 B1 | 4/2003 | Stahurski | |
| 6,554,831 B1 | 4/2003 | Rivard et al. | |
| 6,565,605 B2 | 5/2003 | Goble et al. | |
| 6,579,319 B2 | 6/2003 | Goble et al. | |
| 6,610,091 B1 | 8/2003 | Reiley | |
| 6,616,669 B2 * | 9/2003 | Ogilvie et al. | 606/61 |
| 6,645,207 B2 | 11/2003 | Dixon | |
| 6,669,729 B2 | 12/2003 | Chin | |
| 6,811,567 B2 | 11/2004 | Reiley | |
| 7,011,685 B2 * | 3/2006 | Arnin et al. | 623/17.16 |
| 2002/0007183 A1 | 1/2002 | Lee et al. | |
| 2002/0052603 A1 | 5/2002 | Nichols et al. | |
| 2002/0065557 A1 | 5/2002 | Goble et al. | |
| 2002/0072800 A1 | 6/2002 | Goble et al. | |
| 2002/0095154 A1 * | 7/2002 | Atkinson et al. | 606/61 |
| 2002/0111625 A1 | 8/2002 | Richelsoph et al. | |
| 2002/0123806 A1 | 9/2002 | Reiley | |
| 2002/0133155 A1 * | 9/2002 | Ferree | 606/61 |
| 2002/0138077 A1 | 9/2002 | Ferree | |
| 2002/0143330 A1 | 10/2002 | Shluzas | |
| 2002/0169448 A1 | 11/2002 | Vanacker | |
| 2003/0004572 A1 | 1/2003 | Goble et al. | |
| 2003/0018334 A1 | 1/2003 | Richelsoph et al. | |
| 2003/0023244 A1 | 1/2003 | Richelsoph et al. | |
| 2003/0028192 A1 | 2/2003 | Schar et al. | |
| 2003/0028250 A1 | 2/2003 | Reiley et al. | |
| 2003/0045874 A1 | 3/2003 | Thomas | |
| 2003/0055427 A1 | 3/2003 | Graf | |
| 2003/0083657 A1 | 5/2003 | Drewry et al. | |
| 2003/0109880 A1 | 6/2003 | Shirado et al. | |
| 2003/0114853 A1 | 6/2003 | Burgess et al. | |
| 2003/0135277 A1 | 7/2003 | Bryan et al. | |
| 2003/0153912 A1 | 8/2003 | Graf | |
| 2003/0153917 A1 | 8/2003 | Richelsoph et al. | |
| 2003/0171749 A1 | 9/2003 | Le Couedic et al. | |
| 2003/0171750 A1 | 9/2003 | Chin | |
| 2003/0191470 A1 * | 10/2003 | Ritland | 606/61 |
| 2003/0191532 A1 | 10/2003 | Goble et al. | |
| 2003/0220642 A1 | 11/2003 | Freudiger | |
| 2003/0220643 A1 | 11/2003 | Ferree | |
| 2004/0002708 A1 * | 1/2004 | Ritland | 606/61 |
| 2004/0006342 A1 | 1/2004 | Altarac et al. | |
| 2004/0006391 A1 | 1/2004 | Reiley | |
| 2004/0039385 A1 | 2/2004 | Mazda et al. | |
| 2004/0049188 A1 | 3/2004 | Slivka et al. | |
| 2004/0049189 A1 | 3/2004 | Le Couedic et al. | |
| 2004/0049190 A1 | 3/2004 | Biedermann et al. | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0073215 A1 | 4/2004 | Carli | |
| 2004/0087949 A1 | 5/2004 | Bono et al. | |
| 2004/0111154 A1 | 6/2004 | Reiley | |
| 2004/0116927 A1 | 6/2004 | Graf | |
| 2004/0116928 A1 | 6/2004 | Young et al. | |
| 2004/0133203 A1 | 7/2004 | Young et al. | |
| 2004/0143264 A1 | 7/2004 | McAfee | |
| 2004/0186475 A1 | 9/2004 | Falahee | |
| 2004/0236328 A1 * | 11/2004 | Paul et al. | 606/61 |
| 2004/0236329 A1 | 11/2004 | Panjabi | |
| 2005/0033431 A1 | 2/2005 | Gordon et al. | |
| 2005/0033432 A1 | 2/2005 | Gordon et al. | |
| 2005/0033439 A1 | 2/2005 | Gordon et al. | |
| 2005/0101954 A1 | 5/2005 | Simonson | |
| 2005/0101956 A1 | 5/2005 | Simonson | |
| 2005/0102028 A1 * | 5/2005 | Arnin et al. | 623/17.13 |
| 2005/0113927 A1 | 5/2005 | Malek | |
| 2005/0119657 A1 | 6/2005 | Goldsmith | |
| 2006/0142759 A1 * | 6/2006 | Arnin et al. | 606/61 |
| 2006/0200130 A1 * | 9/2006 | Hawkins et al. | 606/61 |
| 2006/0241757 A1 | 10/2006 | Anderson | |
| 2007/0043356 A1 * | 2/2007 | Timm et al. | 606/61 |
| 2007/0049936 A1 * | 3/2007 | Colleran et al. | 606/61 |
| 2007/0073396 A1 * | 3/2007 | Arnin | 623/17.11 |

FOREIGN PATENT DOCUMENTS

| | | |
|---|---|---|
| DE | 3639810 | 5/1988 |
| EP | 0128058 | 12/1984 |
| EP | 0242708 | 10/1987 |
| EP | 0669109 | 2/1994 |
| EP | 1295566 | 3/2003 |
| FR | 2615095 | 11/1988 |
| FR | 2645427 | 10/1990 |
| FR | 2813782 | 3/2002 |
| FR | 2795622 | 1/2005 |
| FR | 2816195 | 5/2005 |

| | | |
|---|---|---|
| GB | 167228 | 7/1921 |
| GB | 2173104 | 10/1986 |
| GB | 2208476 | 4/1989 |
| WO | 87/00160 | 1/1987 |
| WO | 90/04948 | 5/1990 |
| WO | 91/16020 | 10/1991 |
| WO | WO-01/45576 | 6/2001 |
| WO | WO-02/17803 | 3/2002 |
| WO | 02/30307 | 4/2002 |
| WO | 02/43603 | 6/2002 |
| WO | WO-02/43603 | 6/2002 |
| WO | 02/102259 | 12/2002 |
| WO | WO-02/102259 | 12/2002 |
| WO | 03/007828 | 1/2003 |
| WO | WO-03/007828 | 1/2003 |
| WO | 03/009737 | 2/2003 |
| WO | WO-03/009737 | 2/2003 |
| WO | 2004/024011 | 3/2004 |
| WO | WO-2004/024011 | 3/2004 |
| WO | 2004/034916 | 4/2004 |
| WO | WO-2004/034916 | 4/2004 |

OTHER PUBLICATIONS

"OvationTM Polyaxial System" by Osteotech, Inc., description downloaded from http://www.osteotech.com/prodpoly2.htm; pp. 1-6.

Asher, et al., "A Modular Spinal Rod Linkage System to Provide Rotational Stability", SPINE, vol. 13, No. 3, pp. 272-277, 1998.

Betz, Randall R. et al., DePuy AcroMed Brochure, "Fronterior Anterior Deformity System," Surgical Technique, 21 pages, Aug. 2002.

Carson et al., "Internal Forces and Moments in Transpecular Spine Instrumentation", SPINE, vol. 15, No. 9, pp. 893-901 (1999).

DePuy AcroMed, "CrossOver CrossConnector" brochure, Apr. 2003.

DePuy AcroMed, "Modular Cross Connector (MCC)" brochure, 2000.

Dick et al., "Mechanical Evaluation of Cross-Link Designs in Rigid Pedicle Screw Systems", SPINE, vol. 22, No. 4, pp. 370-375, 1997.

Kaneda, Kiyoshi et al., DePuy AcroMed Brochure "Kaneda SR Anterior Spinal System," Surgical Technique, pp. 1-11, 1999.

Lim, et al., "Biomechanics of Transfixation in Pedicle Screw Instrumentation", SPINE, vol. 21, No. 19, pp. 2224-2229, 1996.

Martin H. Krag, "Biomechanics of Thorocolumbar Spinal Fixation," SPINE, vol. 16, No. 3 Supplement, pp. S84-S99 (1991).

Hitodo, H., "Bone Fixing Device," Patent Abstracts of Japan; Sep. 14, 1999, No. 14; Abstract of JP 11244299.

* cited by examiner

POSTERIOR DYNAMIC STABILIZATION SYSTEMS AND METHODS

BACKGROUND OF THE INVENTION

The vertebrae in a patient's spinal column are linked to one another by the disc and the facet joints, which control movement of the vertebrae relative to one another. Each vertebra has a pair of articulating surfaces located on the left side, and a pair of articulating surfaces located on the right side, and each pair includes a superior articular surface, which faces upward, and an inferior articular surface, which faces downward. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. Damaged, diseased levels in the spine were traditionally fused to one another. While such a technique may relieve pain, it effectively prevents motion between at least two vertebrae. As a result, additional stress may be applied to the adjoining levels, thereby potentially leading to further damage.

More recently, techniques have been developed to restore normal function to the facet joints. One such technique involves covering the facet joint with a cap to preserve the bony and articular structure. Capping techniques, however, are limited in use as they will not remove the source of the pain in osteoarthritic joints. Caps are also disadvantageous as they must be available in a variety of sizes and shapes to accommodate the wide variability in the anatomical morphology of the facets. Caps also have a tendency to loosen over time, potentially resulting in additional damage to the joint and/or the bone support structure containing the cap.

Other techniques for restoring the normal function to the posterior element involve arch replacement, in which superior and inferior prosthetic arches are implanted to extend across the vertebra typically between the spinous process. The arches can articulate relative to one another to replace the articulating function of the facet joints. One drawback of current articulating facet replacement devices, however, is that they require the facet joints to be resected. Moreover, alignment of the articulating surfaces with one another can be challenging.

Accordingly, there remains a need for improved systems and methods that are adapted to mimic the natural function of the facet joints.

BRIEF SUMMARY OF THE INVENTION

The present invention provides various methods and devices for stabilizing adjacent vertebrae in a patient's spinal column. In one exemplary embodiment, a spinal stabilization device is provided having a first cross-connector that is adapted to mate to opposed lateral sides of a first vertebra, a second cross-connector that is adapted to mate to opposed lateral sides of a second vertebra, and a flexible member that is coupled to the first and second cross-connectors and that is adapted to allow movement between first and second adjacent vertebrae coupled to the first and second cross-connectors. In an exemplary embodiment, the flexible member is coupled to the first and second cross-connectors at a fixed position, such that the flexible member does not slide. The flexible member can, however, be adapted to pivot or rotate about the fixed position.

Each cross-connector can have a variety of configurations. In an exemplary embodiment, each cross-connector is substantially rigid, but they can be bendable to allow them to be configured as desired. For example, each cross-connector can be formed from a spinal rod. A variety of techniques can also be used to mate the cross-connectors to adjacent vertebrae. In one embodiment first and second opposed terminal ends of the first cross-connector can couple to first and second bone screws, and first and second opposed terminal ends of the second cross-connector can coupled to third and fourth bone screws.

The flexible member can also have a variety of configurations. In one embodiment, the flexible member can be in the form of an elastomeric spring. For example, the elastomeric spring can include an elastomeric core defining a central opening. A metal spring can be disposed around and mated to the elastomeric core. The shape of the elastomeric spring can also vary, and in one embodiment the elastomeric spring can have a substantially circular shape with a central opening formed therein and with first and second opposed lobes and third and fourth opposed lobes. In another embodiment, the flexible member can be in the form of one or more flexible rods. The flexible rod(s) can be linear or it can have a curved shape. In an exemplary embodiment, first and second flexible rods are coupled to the first and second cross-connectors. The device can also optionally include a flexible connector extending between the first and second flexible rods and adapted to limit extension of the first and second flexible rods. In other embodiments, the flexible member can be in the form of a helical spring, a torsion spring, a flexible mesh material, etc. The flexible member can also couple to the cross-connectors using a variety of techniques. For example, in one embodiment the flexible member can be adapted to rigidly couple to the first and second cross-connectors. In another embodiment, the flexible member can be adapted to pivotally couple to the first and second cross-connectors.

Methods for stabilizing adjacent vertebrae in a spinal column are also provided. In one exemplary embodiment, first and second superior bone screws can be implanted in a superior vertebra, and first and second inferior bone screws can be implanted in an adjacent inferior vertebra. Opposed ends of a superior cross-connector can be connected to the first and second superior bone screws, and opposed ends of an inferior cross-connector can be connected to the first and second inferior bone screws. A flexible member can be coupled to the superior and inferior cross-connectors to allow controlled movement between the adjacent superior and inferior vertebrae.

The flexible member can be coupled to various portions of the superior and inferior cross-connectors. For example, in one embodiment the flexible member can be coupled to a mid-portion of the superior and inferior cross-connectors. In another embodiment, first and second flexible members can be coupled to the superior and inferior cross-connectors at a position between the opposed ends of the superior and inferior cross-connectors but spaced apart from one another. In other embodiments, the flexible member can be adapted to limit extension of the adjacent superior and inferior vertebrae.

An exemplary method can also include coupling a barrier to the superior and inferior cross-connectors to separate tissue overlying the device from tissue underlying the device. The device can also include other features to protect surrounding tissue. For example, at least a portion of the device can be coated with a non-fouling material adapted to minimize cell attachment to the device.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1A:
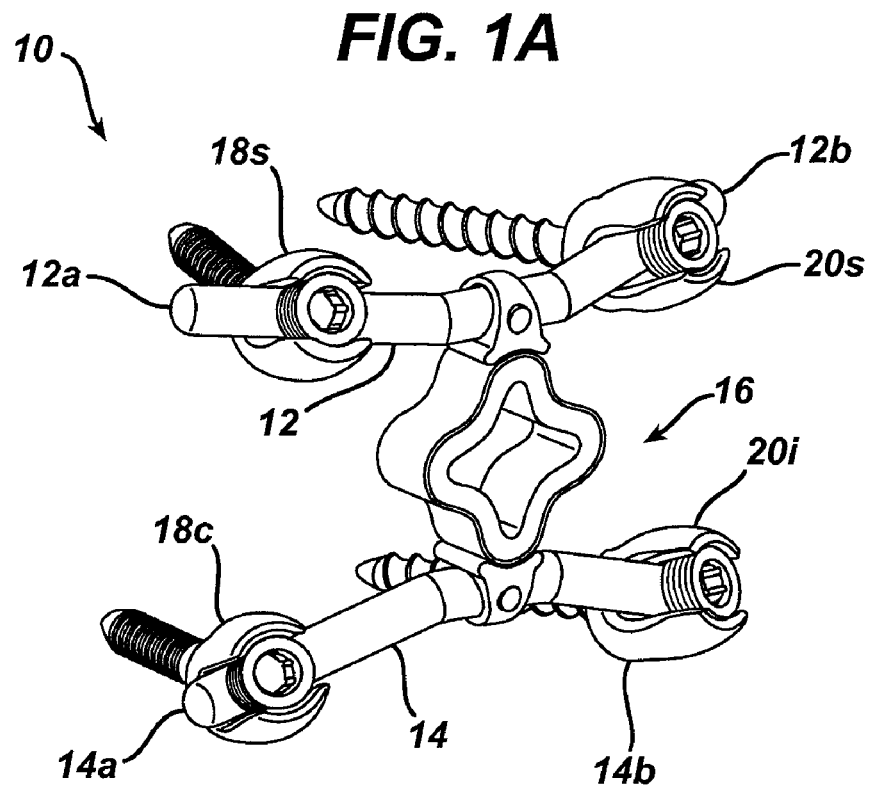
FIG. 1A is a perspective view of one exemplary embodiment of a spinal stabilization device having first and second cross-connectors adapted to mate to opposed lateral sides of adjacent vertebrae, and a flexible member coupled to the first and second cross-connectors.
Figure 1B:
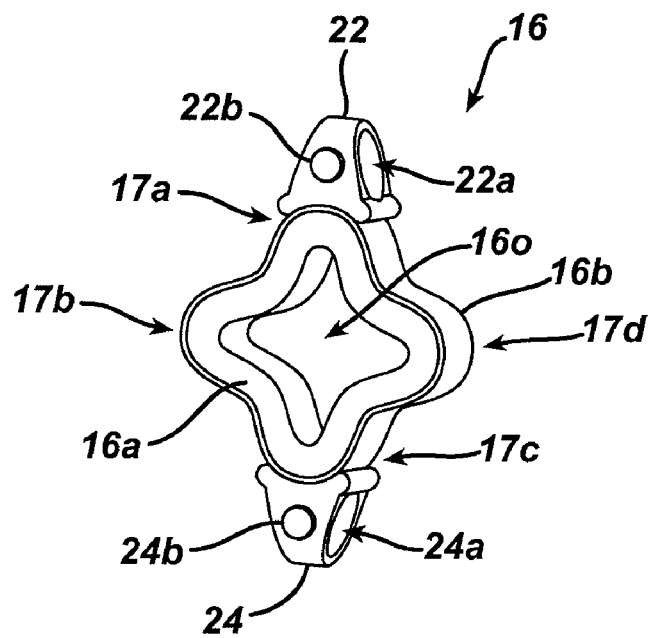
FIG. 1B is a perspective view of the flexible member of the spinal stabilization device shown in FIG. 1A.
Figure 1C:
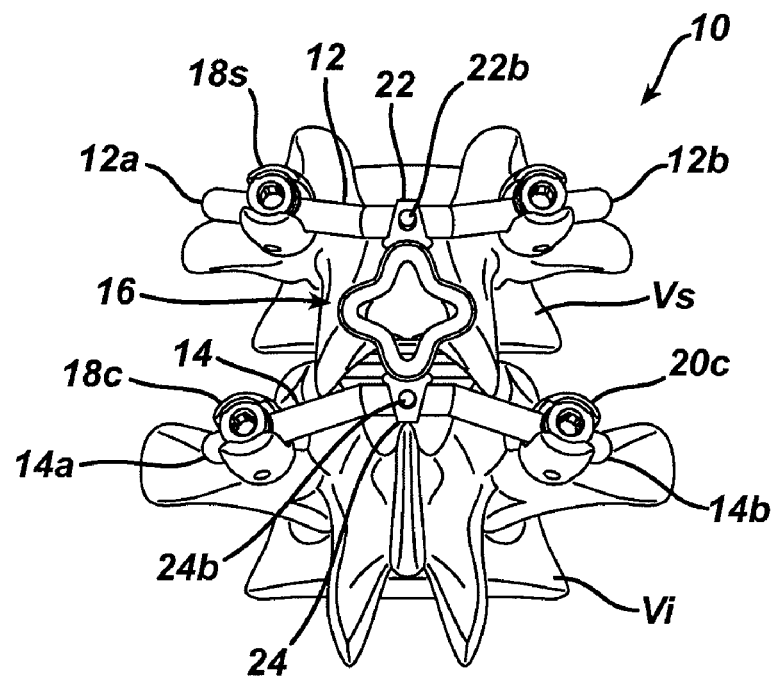
FIG. 1C is a perspective view of the spinal stabilization device shown in FIG. 1A mated to adjacent vertebrae in a spinal column.

FIGS. 1A-1C illustrate one exemplary embodiment of a spinal stabilization device. As shown, the device 10 generally includes a first cross-connector 12 that is adapted to mate to opposed lateral sides of a first vertebra, and a second cross-connector 14 that is adapted to mate to opposed lateral sides of a second adjacent vertebra. The device 10 also includes a flexible member 16 that mates to the cross-connectors 12, 14 to allow controlled movement between the adjacent vertebrae, preferably sharing the load applied to the vertebrae and other posterior elements. In an exemplary embodiment, the flexible member 16 mates directly to the cross-connectors 12, 14, rather than to bone screws or other elements coupled to the cross-connectors. Such a configuration can prevent loosening, such as screw rotation, between the cross-connectors 12, 14 and the adjacent vertebrae coupled thereto. In use, the flexible member 16 is particularly advantageous as it can change in length as well as orientation, thereby accommodating changes in the angulation between adjacent vertebrae.

The first and second cross-connectors 12, 14 can each have a variety of configurations. In the illustrated embodiment, each cross-connector 12, 14 is in the form of a rod that has a length that is configured to allow opposed terminal ends 12a, 12b, 14a, 14b of each cross-connector 12, 14 to mate to opposed lateral sides of a vertebra. Each cross-connector rod 12, 14 can have a linear configuration or can be curved to facilitate positioning of the cross-connectors 12, 14 relative to adjacent vertebrae. The cross-connectors 12, 14 can also be formed from a variety of materials, but preferably the cross-connectors 12, 14 are substantially rigid. They can, however, be bendable to allow a surgeon to adjust the shape of each cross-connector 12, 14 to conform to the patient's anatomy. One suitable exemplary material for forming the cross-connectors 12, 14 is titanium.

Each cross-connector 12, 14 can be mated to opposed lateral sides of a vertebra using a variety of mating techniques know in the art. For example, as shown in FIGS. 1C, first and second superior bone screws 18s, 20s are implanted in opposed lateral sides, e.g., in the pedicles, of a superior vertebra Vs, and first and second inferior bone screws 18i, 20i are implanted in opposed lateral sides, e.g., in the pedicles, of an adjacent inferior vertebra Vi. The bone screws 18s, 20s, 18i, 20i can have virtually any configuration, and they can be monoaxial or polyaxial bone screws. A person skilled in the art will appreciate that, while bone screws 18s, 20s, 18i, 20i are shown, a variety of other techniques can be used to mate each cross-connector 12, 14 to adjacent vertebrae.

As previously indicated, the device 10 can also include a flexible member 16 that mates to the first and second cross-connectors 12, 14. The flexible member 16 can have a variety of configurations, and it can be formed from one or more components. In the embodiment shown in FIGS. 1A-1C, the flexible member 16 is in the form of a composite spring having a substantially circular shape with a central opening 16o formed therein and first, second, third, and fourth lobes 17a, 17b, 17c, 17d formed therearound. The lobes 17a, 17b, 17c, 17d facilitate compression and expansion of the flexible member 16 during movement of the adjacent vertebrae coupled to the device 10. In particular, the first and third lobes 17a, 17c can extend in a superior-inferior direction such that they can mate to the cross-connectors 12, 14, and the second and fourth lobes 17b, 17d can extend in a medial-lateral direction such that they are positioned between the cross-connectors 12, 14. As the cross-connectors 12, 14 are moved toward one another during extension of the adjacent vertebrae Vs, Vi coupled thereto, the second and fourth lobes 17b, 17d will be compressed. Conversely, as the cross-connectors 12, 14 move away from one another during flexion of the adjacent vertebrae Vs, Vi coupled thereto, the second and fourth lobes 17b, 17d will be stretched, thereby elongating the flexible member 16 in a superior-inferior direction.

The materials used to form the flexible member 16 can vary, but as indicated above in an exemplary embodiment the flexible member 16 is in the form of a composite spring. For example, the flexible member 16 can be formed from an elastomeric core 16a having a thin metal spring 16b disposed therearound. The metal spring 16b can be adhered to the core 16a around the periphery thereof. In use, the metal spring 16b generally has a high tensile ultimate strength but a low stiffness, while the elastomeric core 16a can have a higher stiffness but a low tensile ultimate strength. The elastomeric core 16a thus provides stiffness for small movement while the metal spring 16b provides high ultimate strength to the elastomeric core 16a.

As previously indicated, the flexible member 16 is configured to mate to the cross-connectors 12, 14. While a variety of mating techniques, in an exemplary embodiment the flexible member 16 is configured to mate to the cross-connectors 12, 14 at a fixed location, such that the flexible member 16 does not slide relative to the cross-connectors 12, 14. The flexible member 16 can, however, be adapted to pivot or rotate relative to the cross-connectors 12, 14. In the embodiment shown in FIGS. 1A-1C, a first clamp member 22 is fixedly coupled to the first lobe 17a on the flexible member 16, and a second clamp member 24 is fixedly coupled to the third lobe 17c on the flexible member 16. An adhesive or other mating technique can be used to mate the clamp members 22, 24 to the flexible member 16, or alternatively the clamp members 22, 24 can be integrally formed with the flexible member 16. Each clamp member 22, 24 has a generally cylindrical shape with an opening 22a, 24a formed therethrough. The openings 22a, 24a each have an axis that extends parallel to a plane of the flexible member 16 such that the openings 22a, 24a extend in a medial-lateral when implanted to allow the cross-connectors 12, 14 to be slidably disposed therethrough. Each clamp member 22, 24 can also include a bore formed through a sidewall thereof and extending into the opening 22a, 24a for receiving a fastening element, such as a set screw 22b, 24b. The set screws 22b, 24b can be effective to lock the cross-connectors 12, 14 to the clamp members 22, 24, thereby providing a rigid connection and preventing sliding movement of the cross-connectors 12, 14 relative to the flexible member 16. A person skilled in the art will appreciate that a variety of other techniques can be used to mate the flexible member 16 to the cross-connectors 12, 14, including a clamp, hinge, or pivoting connection, etc.

Figure 1D:
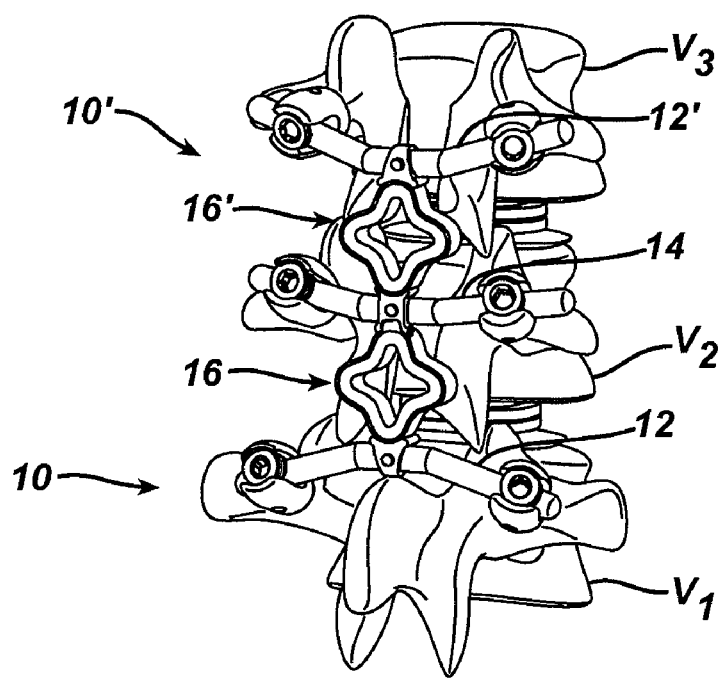
FIG. 1D is a posterior view of a multi-level spinal stabilization device.
Figure 2A:
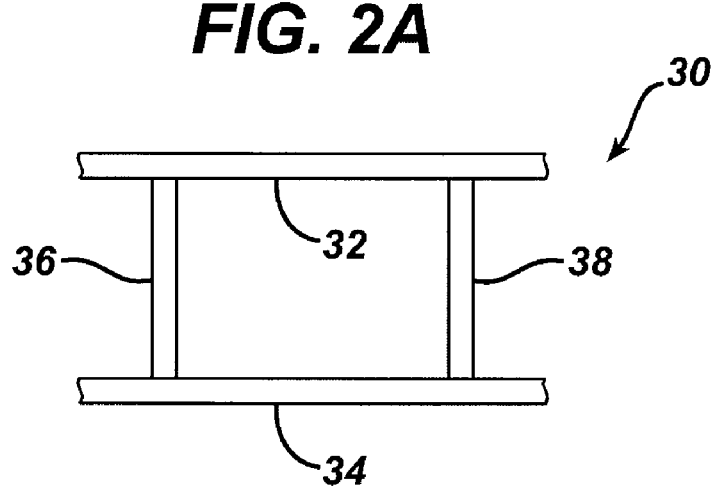
FIG. 2A is a posterior view of another embodiment of a spinal stabilization device having first and second flexible members coupled to first and second cross-connectors.
Figure 2B:
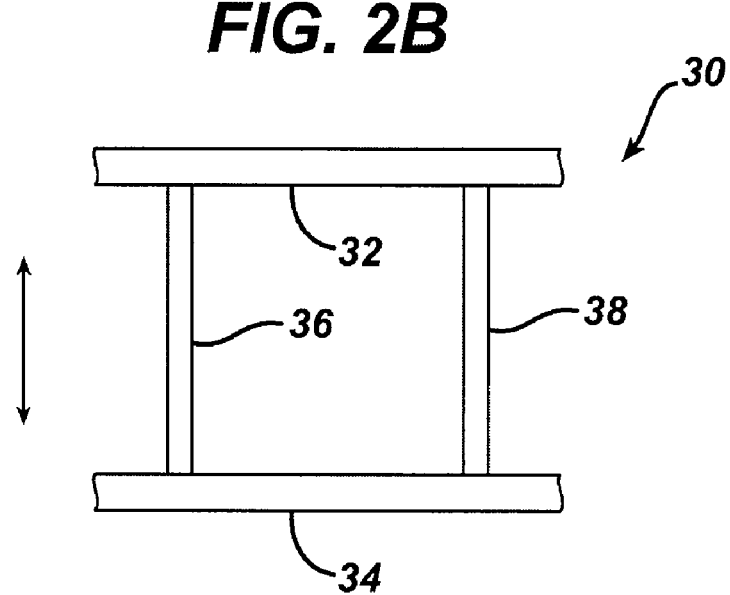
FIG. 2B is a posterior view of the spinal stabilization device shown in FIG. 2A with the cross-connectors moved apart to expand the flexible members.
Figure 3A:
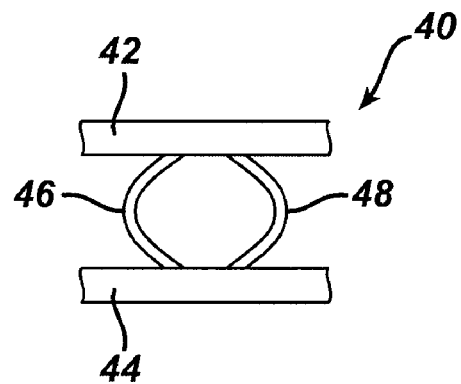
FIG. 3A is a posterior view of another embodiment of a spinal stabilization device having first and second cross-connectors with first and second flexible members curved away from one another and coupled to the cross-connectors at a distance apart from one another.
Figure 3B:
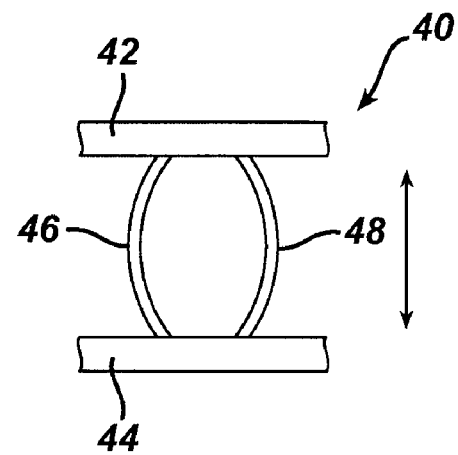
FIG. 3B is a posterior view of the spinal stabilization device shown in FIG. 3A with the cross-connectors moved apart to expand the flexible members.
Figure 4A:
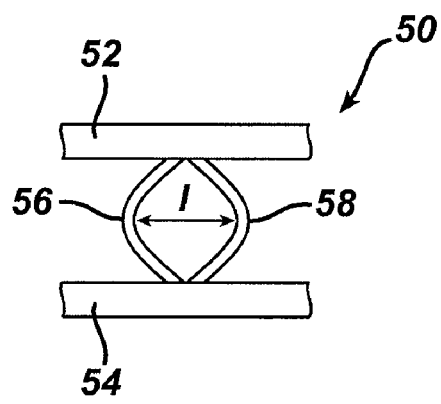
FIG. 4A is a posterior view of another embodiment of a spinal stabilization device having first and second cross-connectors with first and second flexible members curved away from one another and coupled to the cross-connectors at a position adjacent to one another.
Figure 4B:
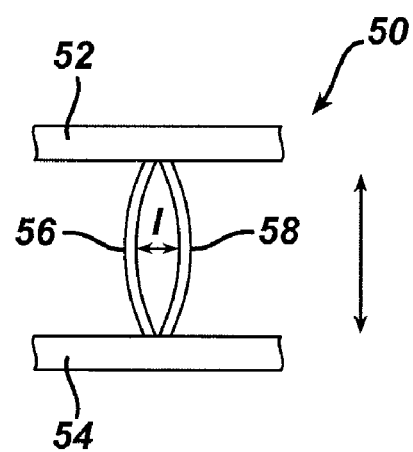
FIG. 4B is a posterior view of the spinal stabilization device shown in FIG. 4A with the cross-connectors moved apart to expand the flexible members.
Figure 5A:
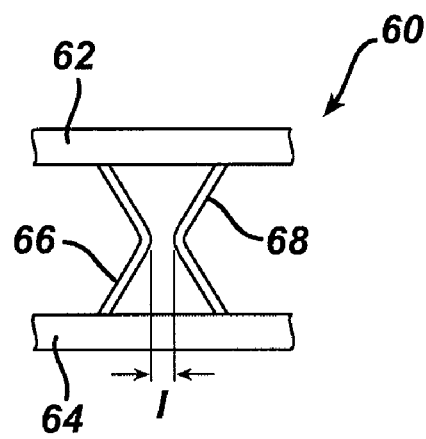
FIG. 5A is a posterior view of another embodiment of a spinal stabilization device having first and second cross-connectors with first and second flexible members curved toward from one another and coupled to the cross-connectors at a distance apart from one another.
Figure 5B:
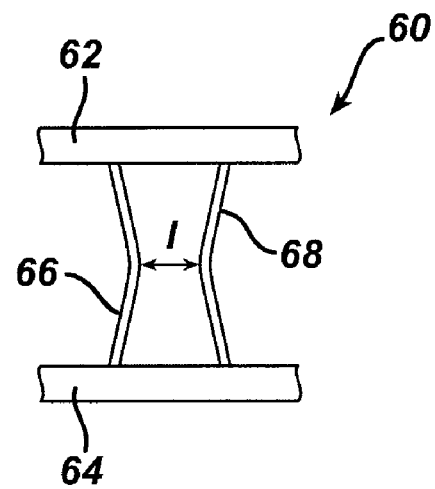
FIG. 5B is a posterior view of the spinal stabilization device shown in FIG. 5A with the cross-connectors moved apart to expand the flexible members.

In use, the flexible member 16 and cross-connector 12, 14 can be pre-mated, or they can be implanted separately. Preferably, the components are pre-mated, however the set screws 22b, 24b are not tightened to allow slidable movement of the flexible member 16. Each cross-connector 12, 14 can be mated to the adjacent vertebrae Vs, Vi using, for example, polyaxial bone screws 18s, 20s, 18i, 20i, as shown in FIG. 1C. The flexible member 16 can then be slid laterally and positioned as desired. While the flexible member 16 can be positioned at various locations along a length of each cross-connector 12, 14, in the illustrated embodiment, the flexible member 16 is mated to a substantial mid-portion of each cross-connector 12, 14. Once properly positioned, the set screws 22b, 24b can be tightened to fixedly attach the flexible member 16 to the cross-connectors 12, 14. Additional devices can be attached to adjacent vertebrae to form a multi-level device. For example, FIG. 1D illustrates three adjacent vertebrae $V_1$, $V_2$, $V_3$, with spinal stabilization device 10 being coupled to the first and second adjacent vertebra $V_1$, $V_2$. A second stabilization 10' is coupled to the third vertebra $V_3$. In particular, a first end of a second flexible member 16' is coupled to the superior cross-connectors 12 of the first device 10, and a second opposed end of the second flexible member 16' is coupled to a third cross-connector 12' mated to the third adjacent vertebrae $V_3$. This can be repeated to stabilize multiple adjacent vertebrae. Movement of the vertebrae $V_1$, $V_2$, $V_3$ will cause the flexible members 16, 16' to flex, thereby providing resistance to the movement and thus stabilizing the adjacent vertebrae $V_1$, $V_2$, $V_3$ and other posterior elements.

Figure 18:
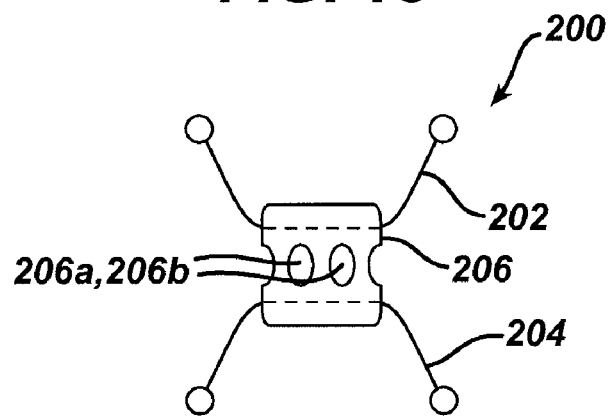
FIG. 18 is a posterior view of yet another embodiment of a spinal stabilization device having first and second cross-connectors coupled by a flexible member having openings formed therethrough.
Figure 19:
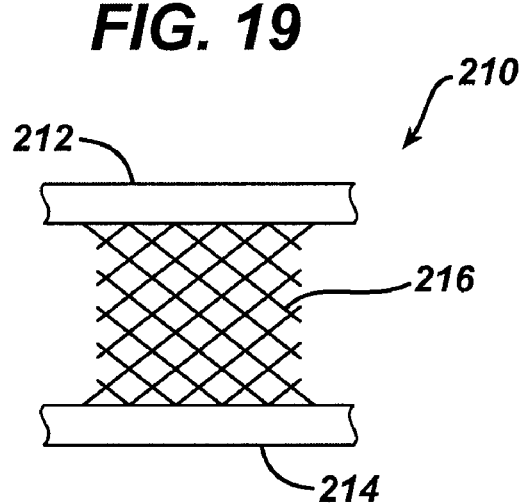
FIG. 19 is a posterior view of one exemplary embodiment of a flexible mesh coupled between first and second cross-connectors.

A person skilled in the art will appreciate that the device 10 can have a variety of other configurations. By way of non-limiting example, FIGS. 2A-18 illustrate various embodiments of flexible members that can be coupled to first and second cross-connectors, and FIG. 19 illustrates another embodiment of first and second cross-connectors for mating to adjacent vertebrae.

Turning first to FIG. 2A-6B, various embodiments of a two component flexible member are shown. In particular, the illustrated spinal stabilization devices 30, 40, 50, 60, 70 each include first and second flexible members 36, 38, 46, 48, 56, 58, 66, 68, 76, 78 that extend between and connect to superior and inferior cross-connectors 32, 34, 42, 44, 52, 54, 62, 64, 72, 74. The flexible members 36, 38, 46, 48, 56, 58, 66, 68, 76, 78 each have a variety of shapes and configurations. In the embodiment shown in FIGS. 2A and 2B, the flexible members 36, 38 are substantially linear. As a result, the flexible members 36, 38 will expand when the cross-connectors 32, 34 move away from one another, i.e., during flexion of the adjacent vertebrae, as shown in FIG. 2B, and they will contract when the cross-connectors 32, 34 return to the resting position. The linear configuration of the flexible members 36, 38 can also be effective to substantially limit or prevent extension of the adjacent vertebrae coupled to the device 30.

Figure 6A:
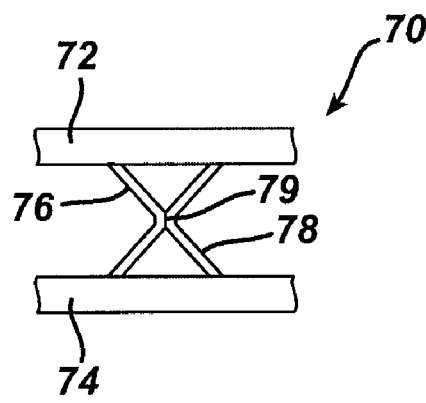
FIG. 6A is a posterior view of another embodiment of a spinal stabilization device having first and second cross-connectors with first and second flexible members curved toward from one another and coupled to the cross-connectors at a position adjacent to one another.
Figure 6B:
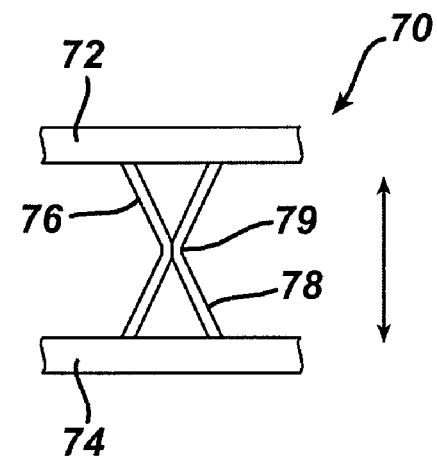
FIG. 6B is a posterior view of the spinal stabilization device shown in FIG. 6A with the cross-connectors moved apart to expand the flexible members.
Figure 7A:
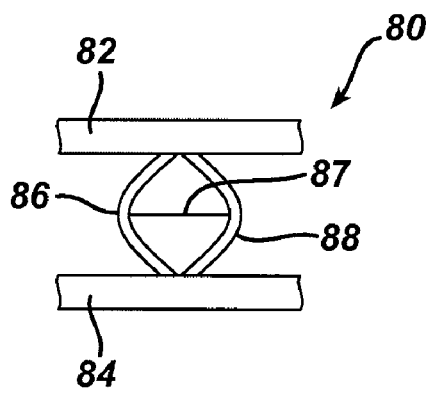
FIG. 7A is a posterior view of a spinal stabilization device according to another embodiment having first and second cross-connectors, first and second flexible members connected to the first and second cross-connectors, and a cable connector coupled between the first and second flexible members.
Figure 7B:
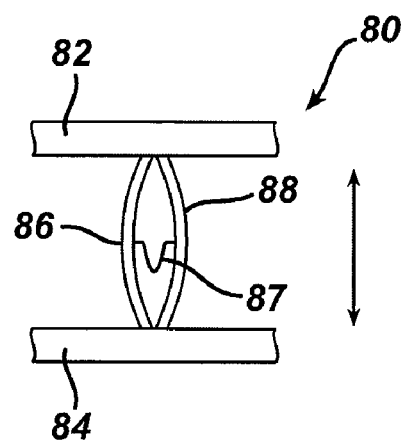
FIG. 7B is a posterior view of the spinal stabilization device shown in FIG. 7A showing the cross-connectors moved apart to extend the flexible members.
Figure 8:
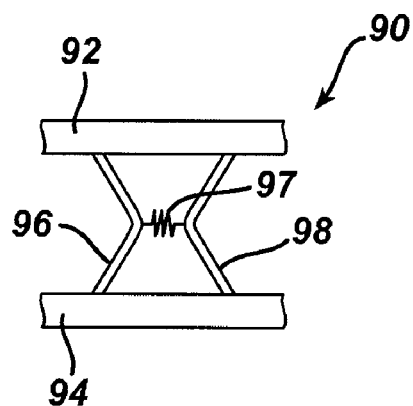
FIG. 8 is a posterior view of another embodiment of a spinal stabilization device having first and second cross-connectors, first and second flexible members connected to the first and second cross-connectors, and a helical spring connector coupled between the first and second flexible members.
Figure 9:
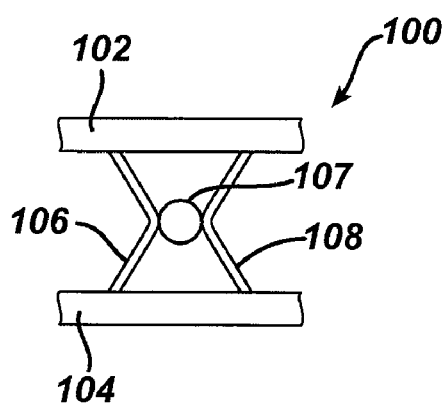
FIG. 9 is a posterior view of another embodiment of a spinal stabilization device having first and second cross-connectors, first and second flexible members connected to the first and second cross-connectors, and a band spring connector coupled between the first and second flexible members.
Figure 10:
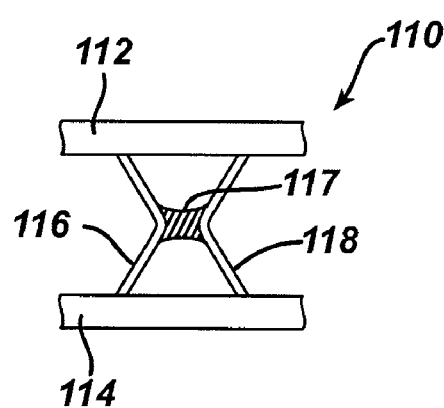
FIG. 10 is a posterior view of another embodiment of a spinal stabilization device having first and second cross-connectors, first and second flexible members connected to the first and second cross-connectors, and a elastomer connector coupled between the first and second flexible members.

In another embodiment, as shown in FIGS. 3A-6B, the flexible members can be pre-shaped to have a curved configuration in the resting state. Curved flexible members, as opposed to linear flexible members, can require less strain to flex, thereby providing a larger range motion. For example, FIGS. 3A-4B illustrate first and second flexible members 46, 48, 56, 58 that are curved away from one another such that a large opening is formed between the flexible members 46, 48, 56, 58. In use, when the cross-connectors 42, 44, 52, 54 move away from one another during flexion of the vertebrae mated thereto, the curved configuration of the flexible members 46, 48, 56, 58 allows the flexible members 46, 48, 56, 58 to straighten, as shown in FIGS. 3B and 4B. Such a configuration provides less resistance during the early stages of flexion than the linear flexible members 36, 38 shown in FIGS. 2A and 2B. As flexion continues, and the curved flexible members 46, 48, 56, 58 become substantially linear, they will begin to stretch thereby providing increased resistance to flexion. FIGS. 5A-6B illustrate first and second flexible members 66, 68, 76, 78 that are curved toward one another such that a mid-portion of each flexible member 66, 68, 76, 78 is close to being in contact with one another. In use, when the cross-connectors 62, 64, 72, 74 move away from one another during flexion of the vertebrae mated thereto, the curved configuration of the flexible members 66, 68, 76, 78 allows the flexible members 66, 68, 76, 78 to straighten, as shown in FIGS. 5B and 6B. Such a configuration provides less resistance during the early stages of flexion than the linear flexible members 36, 38 shown in FIGS. 2A and 2B. As flexion continues, and the curved flexible members 66, 68, 76, 78 become substantially linear, they will begin to stretch thereby providing increased resistance to flexion. Conversely, when the cross-connectors 62, 64, 72, 74 move toward one another, the flexible members 66, 68, 76, 78 will curve toward one another, eventually coming into contact with one another and limiting or prevent further extension of the adjacent vertebrae.

The flexible members 36, 38, 46, 48, 56, 58, 66, 68, 76, 78 in each of the various embodiments shown in FIGS. 2A-6A can also be positioned at various locations relative to one another, e.g., adjacent to one another or a distance apart from one another relative to the cross-connectors 32, 34, 42, 44, 52, 54, 62, 64, 72, 74. The position can be selected to optimize a degree of resistance provided during different movements of the vertebrae. For example, FIGS. 3A-3B and 5A-5B illustrate flexible members 46, 48, 66, 68 that are positioned a distance apart from one another. Such a configuration can provide additional resistance to lateral bending. Conversely, FIGS. 4A-4B and 6A-6B illustrate flexible members 56, 58, 76, 78 that are positioned adjacent to one another. In the embodiment shown in FIGS. 4A and 4B, the terminal ends of the flexible members 56, 58 are substantially in contact with one another or joined. Also, in the embodiment shown in FIGS. 6A and 6B, the mid-portion of the flexible members 76, 78 are substantially in contact with one another or joined. Such a configuration provides less resistance to lateral bending. While not shown, in other embodiments the flexible members can be positioned outside of the bone screws that mate the cross-connectors to the vertebrae, i.e., lateral to the bone screws. Such a configuration may allow the flexible members to be positioned closer to the anterior side of the adjacent vertebrae.

In another embodiment, the flexible members can be coupled to one another, either directly or by a connector, to further increase or decrease the resistance provided by the flexible members during movement of the adjacent vertebrae coupled thereto. As previously discussed, FIGS. 6A and 6B illustrate flexible members 76, 78 connected directly to one another at a mid-portion thereof. The connection will constrain the flexible members 76, 78 and limit the ability of the flexible members 76, 78 to straighten during flexion of the adjacent vertebrae coupled to the device 70, thereby limiting flexion. The connection between the flexible members 76, 78 will also limit or prevent extension of adjacent vertebrae coupled thereto, as was also previously discussed.

As indicated above, the flexible members can alternatively be coupled to one another by a connector. FIGS. 7A-13 illustrate various exemplary embodiments of connectors for mating the flexible members to one another. In the embodiment shown in FIGS. 7A-7B, the device 70 includes a connector that is in the form of a cable or cord 87 that extends between a mid-portion of each flexible member 86, 88. In use, the cable 87 allows straightening of the flexible members 86, 88 when the cross-connectors 82, 84 move away from one another, e.g., during flexion of the adjacent vertebrae coupled thereto. During extension, however, the cable 87 can function as a physical stop preventing the flexible members 86, 88 from being further compressed and thereby preventing further movement of the cross-connectors 82, 84 toward one another.

In other embodiments, rather than providing a physical stop, the connector can provide further resistance to limit extension of the adjacent vertebrae coupled to the device. By way of non-limiting example, FIGS. 8, 9, and 10 each illustrate a spinal stabilization device 90, 100, 110 having a helical or coil spring 97 (FIG. 8), a band spring 107 (FIG. 9), or an elastomeric material 117 (FIG. 10) extending between and coupled to the flexible members 96, 98, 106, 108, 116, 118 to provide resistance to movement of the cross-connectors 92, 94, 102, 104, 112, 114 toward one another and thereby provide resistance to extension of the adjacent vertebrae.

Figure 11:
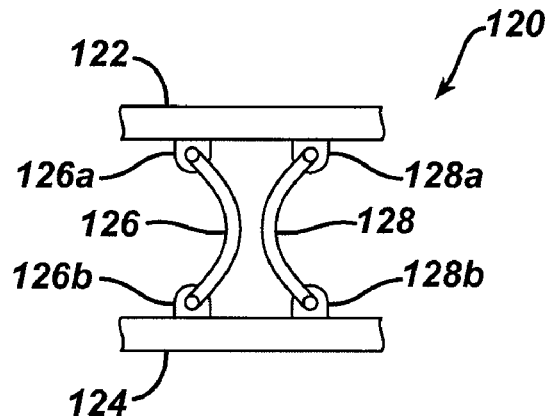
FIG. 11 is a posterior view of yet another embodiment of a spinal stabilization device having first and second flexible members coupled to first and second cross-connectors by hinge joints.
Figure 12:
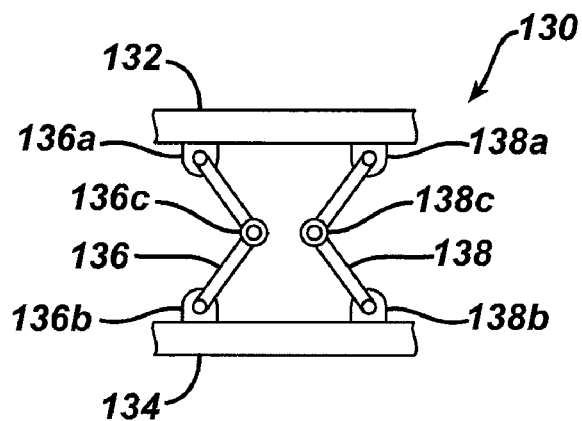
FIG. 12 is a posterior view of a spinal stabilization device according to another embodiment having first and second flexible members having hinge joints formed thereon, and being coupled to first and second cross-connectors by hinge joints.
Figure 13:
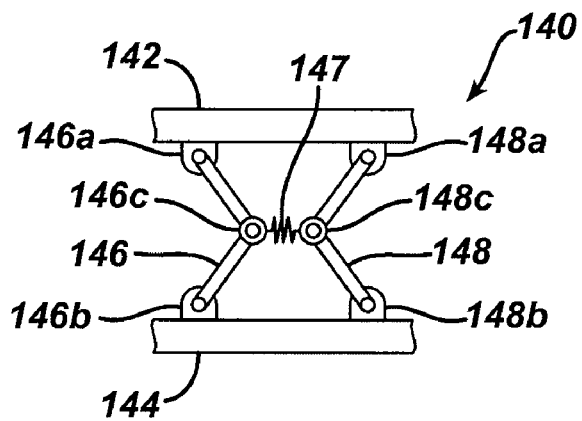
FIG. 13 is a posterior view of another embodiment of a spinal stabilization device having first and second cross-connectors, first and second flexible members connected to the first and second cross-connectors, and a spring coil connector coupled between the first and second flexible members.

The amount of movement of adjacent vertebrae coupled to a spinal stabilization device can also be controlled by varying the connection between the flexible member(s) and the cross-connectors. In particular, the flexible member(s) can be pivotally or hingedly coupled to the cross-connectors to reduce the amount of stress or strain applied to the ends of the flexible member(s), and to allow a greater range of motion between the adjacent vertebrae coupled thereto. FIGS. 11-13 illustrate various exemplary embodiments of stabilization devices 120, 130, 140 having hinge joints 126a, 126b, 128a, 128b, 136a, 136b, 138a, 138b, 146a, 146b, 148a, 148b formed between the flexible members 126, 128, 136, 138, 146, 148 and the cross-connectors 122, 124, 132, 134, 142, 144. In an exemplary embodiment, the hinge joints 126a, 126b, 128a, 128b, 136a, 136b, 138a, 138b, 146a, 146b, 148a, 148b allow pivotal motion in the sagittal plane when the device 120, 130, 140 is implanted. As shown in FIGS. 12 and 13, the flexible members 136, 138, 146, 148 can also optionally include one or more hinge joints 136c, 138c, 146c, 148c formed along a length thereof, e.g., at a mid-portion of each flexible member 136, 138, 146, 148. Such a configuration provides additional flexibility and movement when the device 130, 140 is implanted. The hinge joints 136c, 138c, 146c, 148c formed along a length of each flexible member 136, 138, 146, 148 can also be coupled to one another by a connector. For example, FIG. 13 illustrated a connector 147 in the form of a coil spring extending between and coupled to the hinges joints 146c, 148c formed at the mid-portion of the flexible members 146, 148. A person skilled in the art will appreciate that a variety of techniques can be used to provide a hinge or pivotal joint. The hinge joints in the various embodiments shown in FIGS. 11-13 can also optionally be formed from an elastomeric material, allowing additional stretching to occur between the cross-connectors and the flexible members.

Figure 14A:
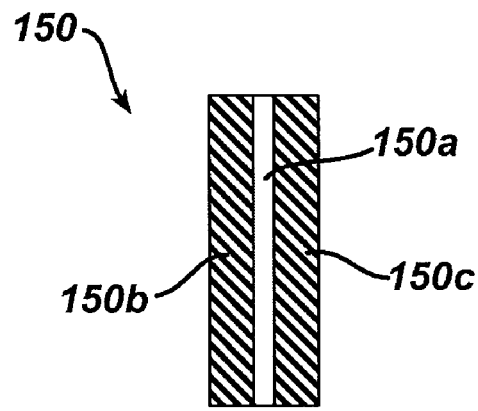
FIG. 14A is an illustration of another embodiment of a flexible member formed from a thin metal band having polymeric material disposed on opposed sides thereof.
Figure 14B:
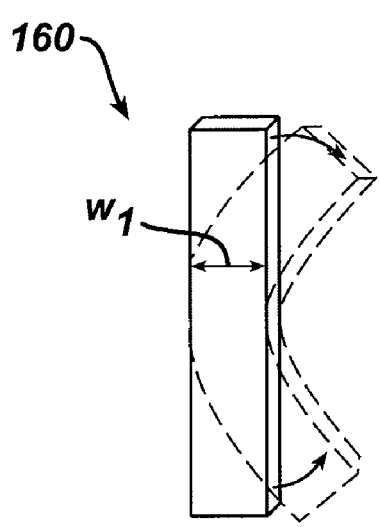
FIG. 14B is a front perspective view of another embodiment of a flexible member having a rectangular configuration.
Figure 14C:
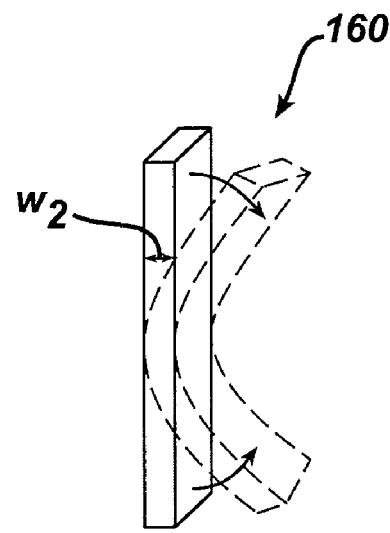
FIG. 14C is a side perspective view of the flexible member shown in FIG. 14B.
Figure 15:
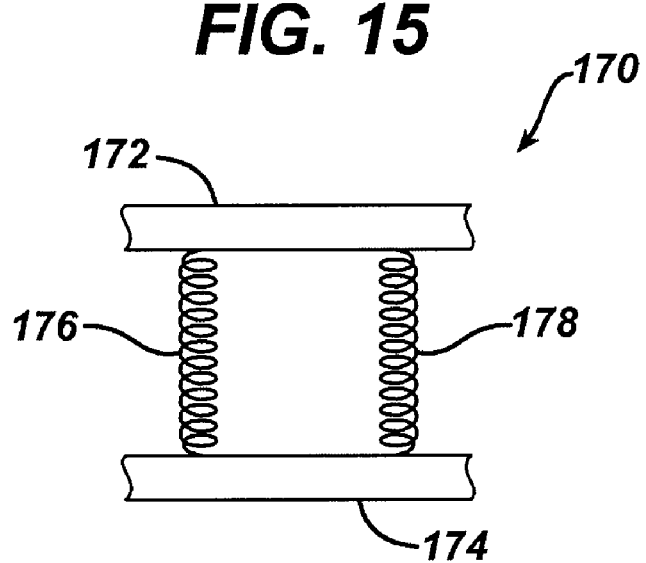
FIG. 15 is a posterior view of another embodiment of a stabilization device having first and second cross-connectors coupled to one another by first and second helical springs.

The particular geometry and properties of each flexible member can also vary to provide a desired amount of resistance during movement of the adjacent vertebrae coupled to the device. For example, as previously indicated the material (s) used to form the flexible members can be selected to obtain a desired result during use of the device. In an exemplary embodiment, the flexible members are formed from a polymeric material, such as polyurethane. The flexible members could also optionally include a support structure to provide rigidity to all or a portion of the flexible members. By way of non-limiting example, FIG. 14A illustrates another embodiment of a flexible member 150 formed from a metal band 150a having an elastomeric material 150b, 150c mated to opposed sides thereof to form a composite beam. Not only can the material be selected to obtain a desired result in use, but the cross-sectional shape can also be selected to control movement as may be desired. For example, a cross-sectional shape of each flexible member can vary to decrease or increase the flexibility when the flexible member is bent in a particular direction. By way of non-limiting example, FIGS. 14B and 14C illustrate a flexible member 160 having a rectangular cross-section with a first width $w_1$ that is greater than a second width $w_2$. The rectangular cross-section will provide a higher amount of resistance when bent in a first direction, as shown in phantom in FIG. 14B, than when bent in a second direction that is substantially transverse to the first direction. The second direction is shown in phantom in FIG. 14C. Such a configuration can, for example, allow flexion and extension of the spine while resisting anterior-posterior shear. The configuration of the flexible members can also vary along a length of the flexible member. For example, a flexible member can be more flexible at a mid-portion than at the end portions, thereby reducing the strain or stress at the mid-portion of the flexible member.

Figure 16:
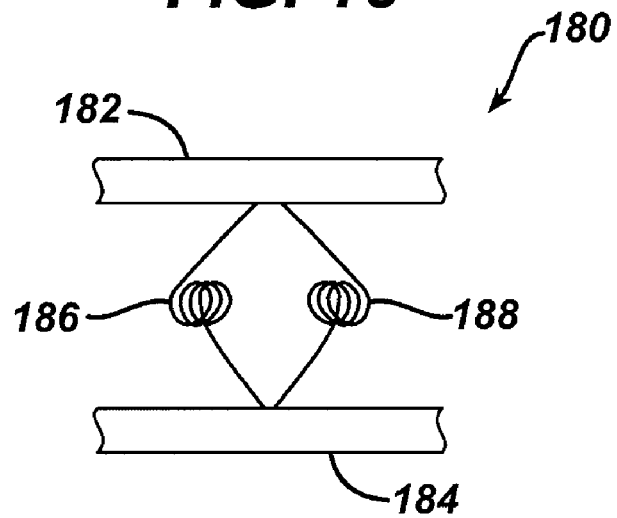
FIG. 16 is a posterior view of another embodiment of a stabilization device having first and second cross-connectors coupled to one another by first and second torsion springs.
Figure 17:
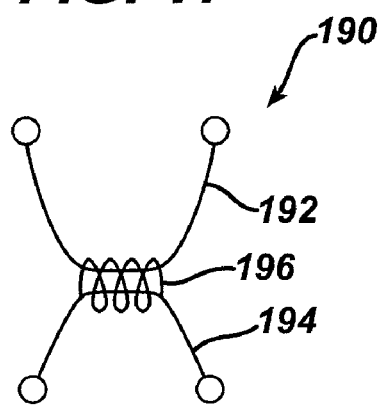
FIG. 17 is a posterior view of another spinal stabilization device having first and second cross-connectors with a coil spring disposed around a portion of each cross-connector.

A person skilled in the art will appreciate that a variety of other techniques can be used to optimize the flexible members to allow or control movement of adjacent vertebrae coupled thereto. FIGS. 15-19 illustrate other embodiments of flexible members for use with a spinal stabilization device. In the embodiment shown in FIG. 15, the device 170 includes two flexible members in the form of helical or coil springs 176, 178 that extend between superior and inferior cross-connectors 172, 174. FIG. 16 illustrates another embodiment of a device 180 having flexible members in the form of springs, however in this embodiment the flexible members are torsion springs 186, 188 that extend between superior and inferior cross-connectors 182, 184. In another embodiment, shown in FIG. 17, the device 190 can include a helical or coil spring 196 that is wrapped around an intermediate portion of each cross-connector 192, 194 to form a flexible member. FIG. 18 illustrates yet another embodiment of a spinal stabilization device 200 having an flexible body 206 that is coupled to superior and inferior cross-connectors 202, 204, and that includes two openings 206a, 206b formed therein to increase the flexibility of the body 206. While two openings are shown, the flexible body 206 can include any number of openings. FIG. 19 illustrates yet another embodiment of a spinal stabilization device 210 having a flexible member 216 extending between superior and inferior cross-connectors 212, 214. In this embodiment, the flexible member 216 is in the form of a mesh material.

Figure 20A:
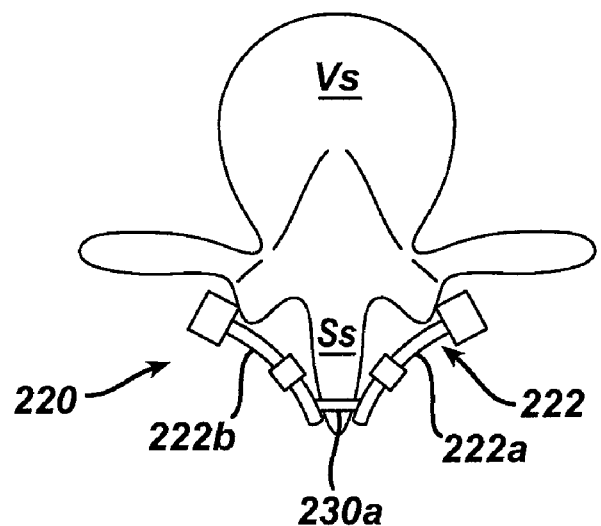
FIG. 20A is a superior view of another embodiment of a spinal stabilization device having cross-connectors mated to the spinous processes of the vertebrae coupled thereto.
Figure 20B:
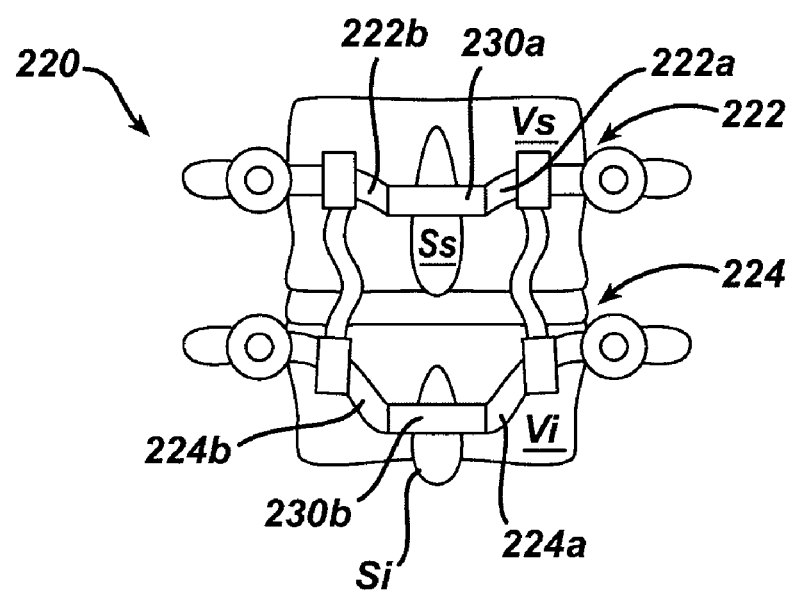
FIG. 20B is a posterior view of the spinal stabilization device and vertebrae shown in FIG. 20A.

In yet another embodiment, the configuration of the cross-connectors can vary to accommodate the anatomy of the spine. For example, as shown in FIGS. 20A and 20B, the stabilization device 220 can include superior and inferior cross-connectors 222, 224 that are adapted to mate to opposed lateral sides of superior and inferior vertebrae Vs, Vi, and that are adapted to mate to the superior and inferior spinous processes Ss, Si of the adjacent vertebrae Vs, Vi. In particular, each cross-connectors 222, 224 can be formed from first and second members 222a, 222b, 224a, 224b that are adapted to extend between a lateral side of the vertebra Vs, Vi and the spinous process Ss, Si. A thru-bore can be formed in one end of each of the first and second members 222a, 222b, 224a, 224b for receiving a bone screw 230a, 230b for mating the ends of the members 222a, 222b, 224a, 224b to the spinous processes Ss, Si and optionally to one another. Such a configuration is particularly advantageous as it does not require removal of the spinous processes Ss, Si, and it prevents large moment on the pedicle screws used to couple the cross-connectors 222, 224 to the opposed lateral sides of the vertebrae Vs, Vi. A person skilled in the art will appreciate that a variety of other techniques can be used to mate the cross-connectors 222, 224 to the spinous processes Ss, Si, and that the cross-connectors 222, 224 can optionally be shaped to fit around and engage the spinous processes Ss, Si rather than mate thereto.

Figure 21:
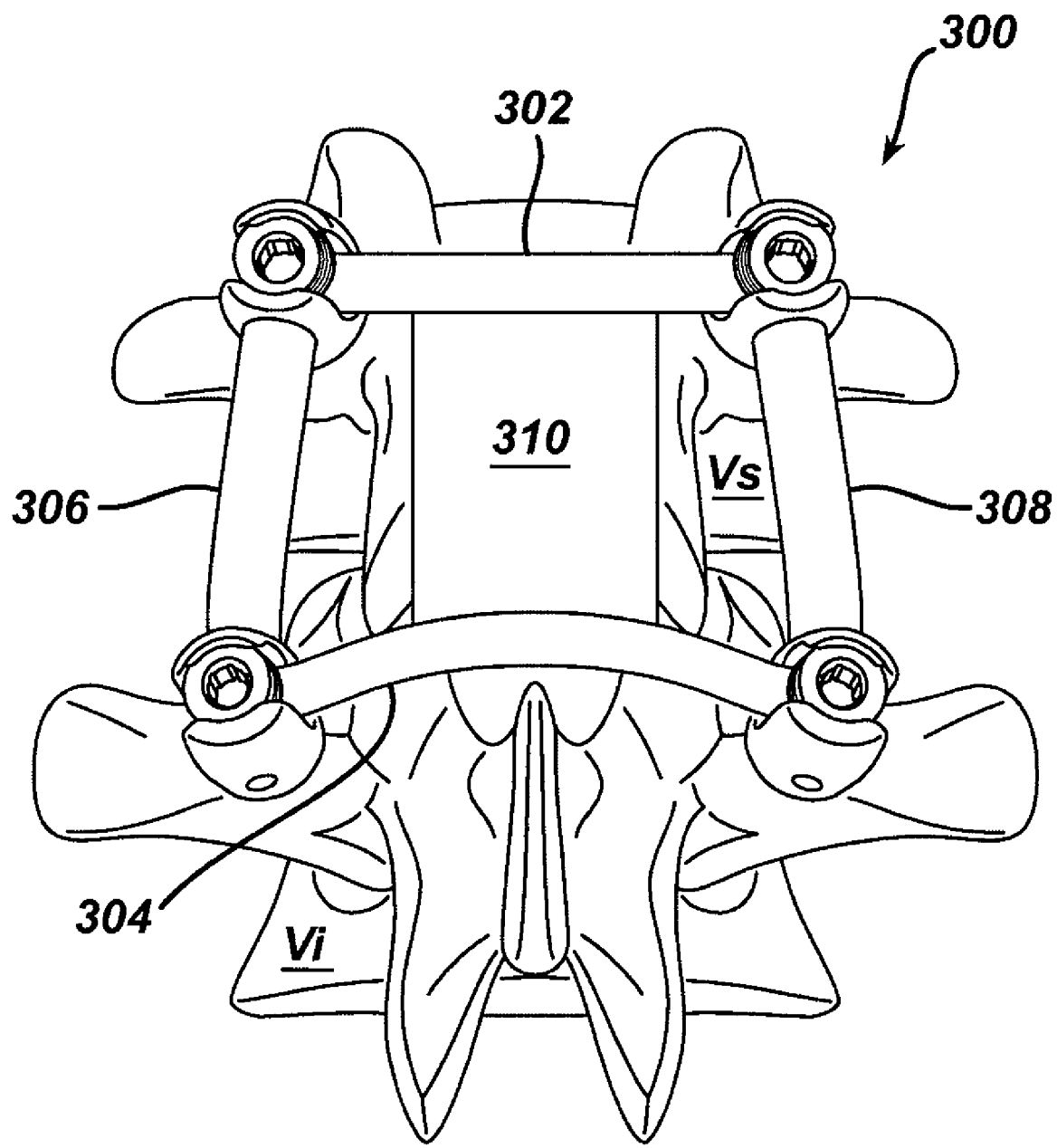
FIG. 21 is a posterior view of a spinal stabilization device coupled to adjacent vertebrae in a spine and having a barrier extending therebetween to separate tissue overlying the device from the tissue underlying the device.

In another exemplary embodiment, the spinal stabilization device can be covered and/or coated with a protective material or barrier that is adapted to protect the device from cell attachment and/or tissue ingrowth, which could potentially interfere with the function of the device. FIG. 21 illustrates one exemplary embodiment of a spinal stabilization device 200 having superior and inferior cross-connectors 302, 304 coupled to adjacent vertebrae Vs, Vi, and first and second flexible members 306, 308 extending between the superior and inferior cross-connectors 302, 304. A protective barrier 310 in the form of an elongate sheet of material extends between the superior and inferior cross-connectors 302, 304 to separate tissue overlying the device 200 from the tissue underlying the device, e.g., the dura mater surrounding the spinal cord. The barrier 310 can also optionally be positioned over the flexible members 306, 308, and/or it can couple to the flexible members 306, 308. The barrier 310 can be mated to the cross-connectors 302, 304 and/or flexible members 306, 308 using a variety of mating techniques known in the art. The barrier 310 can also be formed from a variety of materials, but in one exemplary embodiment the barrier 310 is formed from a polytetrafluoroethylene or Silastic® (polydimethyl siloxane elastomer). In addition or as an alternative to the barrier 210, the flexible members 306, 308 and/or cross-connectors 302, 304 can be covered with a protective material, such as a non-fouling material that inhibits cell attachment and ingrowth.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal stabilization device, comprising:
    a first cross-connector rod having a length that is configured to allow first and second opposed terminal ends to mate to opposed lateral sides of a first vertebra;
    a second cross-connector rod having a length that is configured to allow first and second opposed terminal ends to mate to opposed lateral sides of a second vertebra;
    a flexible member having a substantially circular body with a central opening formed therein, the body having a first lobe formed on an outer surface thereof and extending in superior direction, and a second lobe formed on an outer surface thereof and extending in an inferior direction, the first and second lobes being coupled to first and second clamp members having an opening therethrough for slidably receiving the first and second cross-connector rods such that the flexible member is at a fixed position on each of the first and second cross-connector rods, wherein the first and second lobes are configured move relative to one another to allow movement between first and second adjacent vertebrae coupled to the first and second cross-connector rods; and
    first and second bone screws coupled to the first and second opposed terminal ends of the first cross-connector rod, and third and fourth bone screws coupled to the first and second opposed terminal ends of the second cross-connector rod.

2. The device of claim 1, wherein at least one of the first and second cross-connector rods is bendable.

3. The device of claim 1, wherein at least one of the first and second cross-connector rods is rigid.

4. The device of claim 1, wherein the body comprises an elastomeric spring.

5. The device of claim 1, wherein the body is formed from a composite made from two different materials.

6. The device of claim 5, wherein the body includes an elastomeric core defining the central opening, and a metal spring disposed around and mated to the elastomeric core.

7. The device of claim 6, wherein the metal spring has a shape that corresponds to a shape of the elastomeric core such that the metal spring conforms to an outer surface of the elastomeric core.

8. The device of claim 1, wherein the flexible member has a cross-sectional shape that is adapted to provide a first resistance when the flexible member is flexed in a first direction, and a second resistance when the flexible member is flexed in a second opposite direction, the first and second resistances differing from one another.

9. The device of claim 1, wherein at least a portion of the device is coated with a non-fouling material adapted to minimize cell attachment to the device.

10. The device of claim 1, wherein the first and second cross-connector rods each include a first portion adapted to extend from a first lateral side of a vertebra and to mate to a spinous process, and a second portion adapted to extend from a second lateral side of a vertebra and to mate to a spinous process.

11. The device of claim 1, wherein each clamp member includes a bore for receiving a fastener to lock the clamp member relative to the first and second cross-connector rods.

12. A spinal stabilization device, comprising:
    a first cross-connector having opposed ends configured to mate to opposed lateral sides of a first vertebra;
    a second cross-connector having opposed ends configured to mate to opposed lateral sides of a second vertebra; and
    a flexible member including first and second clamp members having an opening therethrough for receiving the first and second cross-connectors such that the flexible member is at a fixed position on each of the first and second cross-connectors, the flexible member including an elastomeric core having an opening formed therein and first, second, third, and fourth lobes formed on an outer surface thereof, the first and third lobes extending in a superior-inferior direction and the second and fourth lobes extending in a medial-lateral direction such that the elastomeric core is configured to allow movement between first and second adjacent vertebrae coupled to the first and second cross-connectors.

13. The spinal stabilization device of claim 12, wherein the flexible member is formed from a composite made from two different materials.

14. The spinal stabilization device of claim 12, further comprising a metal spring disposed around a periphery of the elastomeric core.

* * * * *